United States Patent
Tang et al.

(10) Patent No.: US 11,241,498 B2
(45) Date of Patent: Feb. 8, 2022

(54) ROOM TEMPERATURE STABLE LYOPHILIZED PROTEIN

(71) Applicant: Regeneron Pharmaceuticals, Inc., Tarrytown, NY (US)

(72) Inventors: Xiaolin Tang, Old Tappan, NJ (US); David Brett Ludwig, Saratoga, NY (US)

(73) Assignee: Regeneran Pharmaceuticals, Inc., Tarrytown, NY (US)

( * ) Notice: Subject to any disclaimer, the term of this patent is extended or adjusted under 35 U.S.C. 154(b) by 0 days.

(21) Appl. No.: 16/655,634

(22) Filed: Oct. 17, 2019

(65) Prior Publication Data
US 2020/0046834 A1   Feb. 13, 2020

Related U.S. Application Data

(62) Division of application No. 15/727,457, filed on Oct. 6, 2017.

(60) Provisional application No. 62/405,610, filed on Oct. 7, 2016.

(51) Int. Cl.
| | | |
|---|---|---|
| *A61K 39/395* | (2006.01) |
| *A61K 9/08* | (2006.01) |
| *A61K 9/00* | (2006.01) |
| *A61J 1/14* | (2006.01) |
| *A61K 9/19* | (2006.01) |
| *A61K 47/02* | (2006.01) |
| *A61K 47/10* | (2017.01) |
| *A61K 47/18* | (2017.01) |
| *A61K 47/26* | (2006.01) |
| *A61K 38/00* | (2006.01) |

(52) U.S. Cl.
CPC ....... *A61K 39/39591* (2013.01); *A61J 1/1412* (2013.01); *A61K 9/0019* (2013.01); *A61K 9/08* (2013.01); *A61K 9/19* (2013.01); *A61K 47/02* (2013.01); *A61K 47/10* (2013.01); *A61K 47/183* (2013.01); *A61K 47/26* (2013.01); *A61K 38/00* (2013.01)

(58) Field of Classification Search
None
See application file for complete search history.

(56) References Cited

U.S. PATENT DOCUMENTS

| | | | |
|---|---|---|---|
| 2009/0208492 A1 | 8/2009 | O'Connor et al. | |
| 2012/0114646 A1* | 5/2012 | Tchessalov | A61P 37/00 424/134.1 |
| 2012/0282249 A1* | 11/2012 | Fox | A61P 1/04 424/133.1 |

* cited by examiner

*Primary Examiner* — Yunsoo Kim
(74) *Attorney, Agent, or Firm* — Kramer Levin Naftalis & Frankel LLP

(57) ABSTRACT

Stable lyophilized therapeutic protein compositions and their methods of manufacture are provided. Specifically, the use of water as a solid cake plasticizer and protein stabilizer is described. Also, the inclusion of a multicomponent stabilizer comprising a larger molecular entity and a smaller molecular entity is described. Also, the inclusion of post-drying annealing under certain conditions improves protein stability. Proteins are predicted to remain stable over 24 months at 25° C.

16 Claims, 13 Drawing Sheets

ROOM TEMPERATURE STABLE LYOPHILIZED PROTEIN

CROSS-REFERENCE TO RELATED APPLICATIONS

Figure 1:
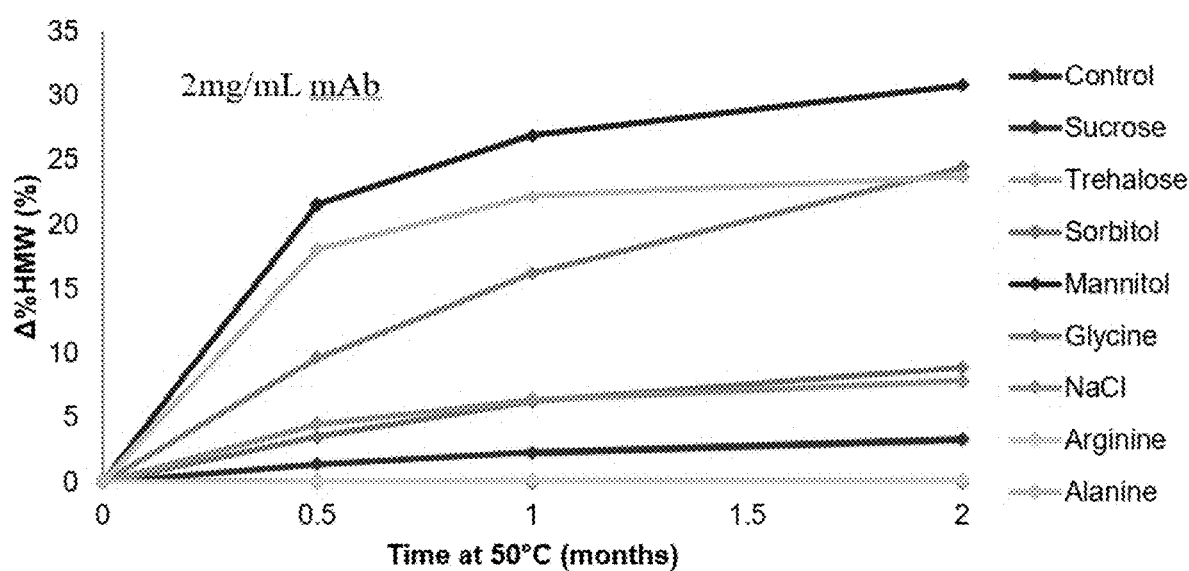

This application is a continuation of U.S. patent application Ser. No. 15/727,457, filed on Oct. 6, 2017 which claims the benefit of U.S. Provisional Patent Application No. 62/405,610, filed on Oct. 7, 2016. The contents of each of these applications are incorporated by reference in their entireties.

FIELD

The present invention relates generally to the field of pharmaceutical formulation of biological molecules. Specifically, the present invention relates to stable lyophilized therapeutic protein formulations.

BACKGROUND

Therapeutic macromolecules, such as antibodies and receptor Fc-fusion proteins, must be formulated in a manner that not only makes the molecules suitable for administration to patients, but also maintains their stability during long term storage. For example, therapeutic proteins (e.g., antibodies) in liquid solution are prone to aggregation, chemical modifications, or other forms of degradation unless the solution is formulated properly. The stability of a therapeutic protein in liquid formulation depends not only on the kinds of excipients used in the formulation, and the amounts and proportions of those excipients relative to one another, but also on the concentration of the soluble protein and the method of manufacturing. Considerations aside from stability must also be taken into account when preparing a therapeutic protein formulation. Those considerations include the viscosity of the solution and the concentration of antibody that can be accommodated by a given formulation. Thus, when formulating a therapeutic protein, great care must be taken to arrive at a formulation that remains stable over time at storage temperature, contains an adequate concentration of antibody or other therapeutic protein, and possesses other properties which enable the formulation to be conveniently administered to patients.

Liquid formulations of therapeutic proteins are generally designed to provide long term stability to the protein when frozen or refrigerated, but often fail to provide long term stability at room temperature. One solution known in the art to preserve the stability and retain therapeutic activity of the protein is to lyophilize the molecule. Lyophilization (freeze drying under controlled conditions) is commonly used for long-term storage of proteins. The lyophilized protein is substantially resistant to degradation, such as aggregation, oxidation, and other degenerative processes while in the freeze-dried state (see, for example, U.S. Pat. No. 6,436,897, Danko et al.). Lyophilization provides a dry "cake" that remains relatively stable at room temperature for a relatively long period of time. Room temperature stability is especially important in storing and distributing therapeutic proteins around the world, especially in places where electricity and refrigeration are not reliable.

Lyoprotectants (a.k.a. stabilizers), such as sucrose and trehalose, are often included in pre-lyophilization formulations to protect the protein against denaturation during the freeze-drying process. Plasticizers may also be included to decrease global relaxation time and in some cases may help to preserve the native structure of proteins. Plasticizers include sugar alcohols like sorbitol and glycerol, other polyols, and small amounts of water.

In studies designed to optimize storage of lyophilized proteins at 5° C., Chang et al. investigated the effect of plasticizers on the stability of protein formulations. In lyophilization cakes that contained a weight ratio of 1:1 sucrose to protein (protein at 40 mg/mL pre-lyophilized) and no additional plasticizers the aggregation rate constant during a month at 50° C. was reportedly over 1.5% at 2.4% water content and around 2% at 3.3% water content (Id. at 1451, FIG. 4). (Chang et al., "Effect of Sorbitol and Residual Moisture on the Stability of Lyophilized Antibodies: Implications for the Mechanism of Protein Stabilization in the Solid State," J. Pharma. Sci. 94(7): 1445-1454, (2005). The experiment was also run for at 40° C. and 25° C. with data presented for only the harshest of the three stress conditions. Chang et al. noted rare examples of documented cases of optimal storage stability at intermediate moisture content and suggested that residual moisture content should be optimized during formulation development rather than something that simply has to be minimized. (Id. at 1451; see also Breen et. al., "Effect of Moisture on the Stability of a Lyophilized Humanized Monoclonal Antibody Formulation," Pharma. Res. 18(9):1345-1353 (2001).) High moisture levels were shown in all of the studies cited by Chang et al. to decrease the chemical stability of the formulations. (Hsu et al. "Determining the Optimum residual Moisture in Lyophilized Protein Pharmaceuticals," Develop. Biol. Standard 74:255-271 (1991).)

None of those studies suggest long term stability (over a year, two years, or three years or more) at a temperature above 5° C., let alone 25° C., even for the formulations tested.

Lyophilized formulations of biotherapeutic drugs have demonstrated long term stability under certain conditions. Kallmeyer et al., WO1998022136A2, describes stable lyophilized antibody formulations of low concentration (e.g., up to 8 mg/ml pre-lyophilized solution) that contain among other excipients a sugar (up to 200 mg/ml post-reconstitution, e.g., sucrose, lactose, maltose, raffinose, trehalose), an amino acid (1-100 mg/ml pre-lyophilized, e.g., arginine, lysine, ornithine), a surfactant (0.05 to 0.5 mg/ml post-reconstitution, e.g., polysorbates and polyoxyethylene-polyoxypropylene polymers), and optionally a buffer (10-20 mM post-reconstitution, e.g., phosphate, acetate, citrate) and/or an isotonizing agent (e.g., NaCl, no more than 30 mM post-reconstitution). Kallmeyer discloses that the lyophilizate that can be stored at room temperature (e.g., 18-23° C.) for up to two years while remaining stable. Here, stability is demonstrated by very low to no particulate formation in reconstituted lyophilizate, e.g., less than 6000 particles of more than 10 microns in size, or less than 600 particles of more than 25 microns in size.

Dix el al., WO2006104852A2, describe a stable lyophilized VEGF-Trap (a.k.a. aflibercept) formulation that maintains biological activity for at least three months. That application discloses the pre-lyophilized solution containing 5-75 mg/ml trap molecule, 5-50 mM histidine buffer, 0.1-3% polyethylene glycol (PEG; stabilizer), 0.25-3% glycine (as a bulking agent), and 0.5-6% sucrose (as a stabilizer). Optionally, the pre-lyophilized solution contains citrate buffer (0.05 mM) and/or 0.003% to 0.005% polysorbate.

In addition to lyophilized protein formulations, spray drying has also been employed to make dry protein formulations. Chen and Walsh (WO201307506A1) disclose dry micronized protein particles having a range of diameter of from two (2) to 30 microns, and a median diameter of about 10 to 12 microns, and in some cases about 6 to about 7 microns. These particles can be subsequently coated with polymer to further stabilize the protein and enable the extended release of the protein over time in an aqueous environment. The pre-processed protein solution from which the micronized particles were formed contained either (1) 25 mg/ml protein and 0.1% polysorbate, (2) 25 mg/ml protein, or (3) 50 mg/ml protein, 10 mM phosphate, and 2% sucrose. The protein contained within the polymer coated micronized protein particles were demonstrated to remain stable for at least 14 days.

Post-drying annealing of a protein lyophilizate was shown at 50° C. to result in an initial antibody aggregation to greater than 4% and the aggregation rate constant was about 2% aggregation per month. (See Wang et al., "The Impact of Thermal Treatment on the Stability of Freeze-Dried Amorphous Pharmaceuticals: II. Aggregation in an IgG1 Fusion Protein," 99(2) J. Pharma. Sci. 683-700 (2010).) While the US FDA might allow marketing of a formulation with initial aggregation at 4%, that rate of aggregation over time would be unacceptable for a marketed pharmaceutical formulation. There should be no visible change in a pharmaceutical formulation during its shelf life.

There remains a need for versatile dry protein formulations that remain stable over an extended period of time at room temperature. Versatile dry protein formulations are amenable to reconstitution for use as a liquid formulation, for combining with polymers to make extended release formulations or devices, and for implanting or delivering via a myriad of other routes. Applicants have developed an improved stable protein lyophilizate and method of making it.

SUMMARY

This disclosure provides a method of preparing a lyophilized cake, comprising: preparing a peptide or protein formulation and subjecting the peptide or protein formulation to lyophilization to produce a lyophilized cake; wherein the peptide or protein formulation comprises a peptide or a protein. In some aspects, the method of preparing a lyophilized cake further comprises subjecting the lyophilized cake to post-lyophilization annealing. In some aspects, the peptide or protein formulation further comprises a stabilizer, a cryo-protectant, a bulking agent, a plasticizer, or a combination thereof. In some aspects, the stabilizer is a hydrogen bond replacing agent, such as polyol, sucrose, trehalose, or amino acid. In some aspects, the cryo-protectant is surfactant, sugar, salt or amino acid; the bulking agent is mannitol, glycine or combinations thereof; and the plasticizer is water or glycine; wherein a concentration of the bulking agent is less than 2%.

In some aspects, the bulking agent is in crystalline state in the lyophilized cake. In some further aspects, the stabilizer or the cryo-protectant is in amorphous state in the lyophilized cake. In some exemplary embodiments, the peptide or protein can be an antibody, an antibody fragment, a Fab region of an antibody, an antibody-drug conjugate, a fusion protein, a protein pharmaceutical product or a drug.

In some exemplary embodiments, the concentration of the peptide or protein in the peptide or protein formulation is at least 100 mg/mL, wherein the peptide or protein formulation further comprises a viscosity reducer.

In some aspects, the peptide or protein formulation is an isotonic formulation, wherein the peptide or protein formulation comprises 9% sucrose, wherein the isotonic formulation further comprises arginine. In some aspects, the peptide or protein formulation comprises sucrose and mannitol. In some aspects, the peptide or protein formulation comprises sucrose and glycine.

The disclosure, at least in part, provides a lyophilized cake prepared by the method of preparing a lyophilized cake of the present application. In some exemplary embodiments, the lyophilized cake prepared by the method of preparing a lyophilized cake of the present application comprises about 3-5% water and is stable under the storage condition at room temperature.

These, and other, aspects of the invention will be better appreciated and understood when considered in conjunction with the following description and the accompanying drawings. The following description, while indicating various embodiments and numerous specific details thereof, is given by way of illustration and not of limitation. Many substitutions, modifications, additions, or rearrangements may be made within the scope of the invention.

BRIEF DESCRIPTION OF THE DRAWINGS

FIG. 1 shows screening of various stabilizers for the monoclonal antibody formulations which had low protein concentrations at 2 mg/mL by monitoring the formation of high molecular weight (HMW) aggregations at storage condition of 50° C. for various time periods within 0-2 months according to an exemplary embodiment.

FIG. 2 shows the stabilities of lyophilized mAb formulations containing various stabilizers using 2 mg/mL mAb formulations for 13 months at 25° C. according to an exemplary embodiment.

FIG. 3 shows screening of various stabilizers for the monoclonal antibody formulations which had high protein concentrations at 150 mg/mL by monitoring the formation of HMW aggregations at storage condition of 50° C. for various time periods within 0-2 months according to an exemplary embodiment.

FIG. 4 shows the studies of protein conformation using FT-IR (Fourier transform infrared spectroscopy) spectrometer system from Bruker Optics Inc. using 150 mg/mL lyophilized mAb formulations according to an exemplary embodiment.

FIG. 5 shows the results for testing various concentrations of sucrose for improving the stabilities of the lyophilized protein formulations containing 150 mg/mL mAb according to an exemplary embodiment. The stabilities of the lyophilized protein formulations were monitored by detecting the formation of HMW aggregations according to an exemplary embodiment.

FIG. 6 shows the results for testing various concentrations of arginine for improving the stabilities of the lyophilized protein formulations containing 150 mg/mL mAb according to an exemplary embodiment. The stabilities of the lyophilized protein formulations were monitored by detecting the formation of HMW aggregations according to an exemplary embodiment.

FIG. 7 shows the results for testing various ratios of sucrose to mannitol for improving the stabilities of the lyophilized protein formulations containing 150 mg/mL mAb according to an exemplary embodiment. The stabilities of the lyophilized protein formulations were monitored by detecting the formation of HMW aggregations at different storage temperatures according to an exemplary embodiment.

FIG. 8 shows the results for testing various ratios of sucrose to glycine for improving the stabilities of the lyophilized protein formulations containing 150 mg/mL mAb according to an exemplary embodiment. The stabilities of the lyophilized protein formulations were monitored by detecting the formation of HMW aggregations at different storage temperatures according to an exemplary embodiment.

Figure 9:
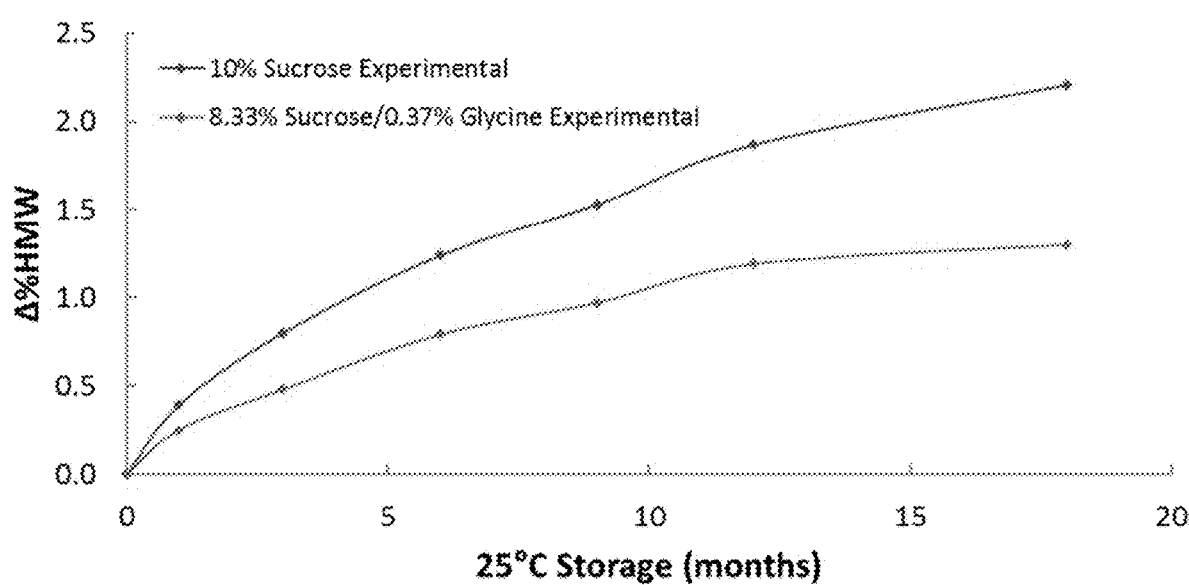

FIG. 9 shows the results for side-by-side comparison between 10% sucrose and an optimal ratio of sucrose to glycine at 8.33% sucrose/0.37% glycine according to an exemplary embodiment. MAB1 monoclonal antibody isotonic formulations at 150 mg/mL were prepared in 10 mM histidine, 0.1% polysorbate-80, pH 5.8 with 10% sucrose or with 8.33% sucrose/0.37% glycine according to an exemplary embodiment.

Figure 10:
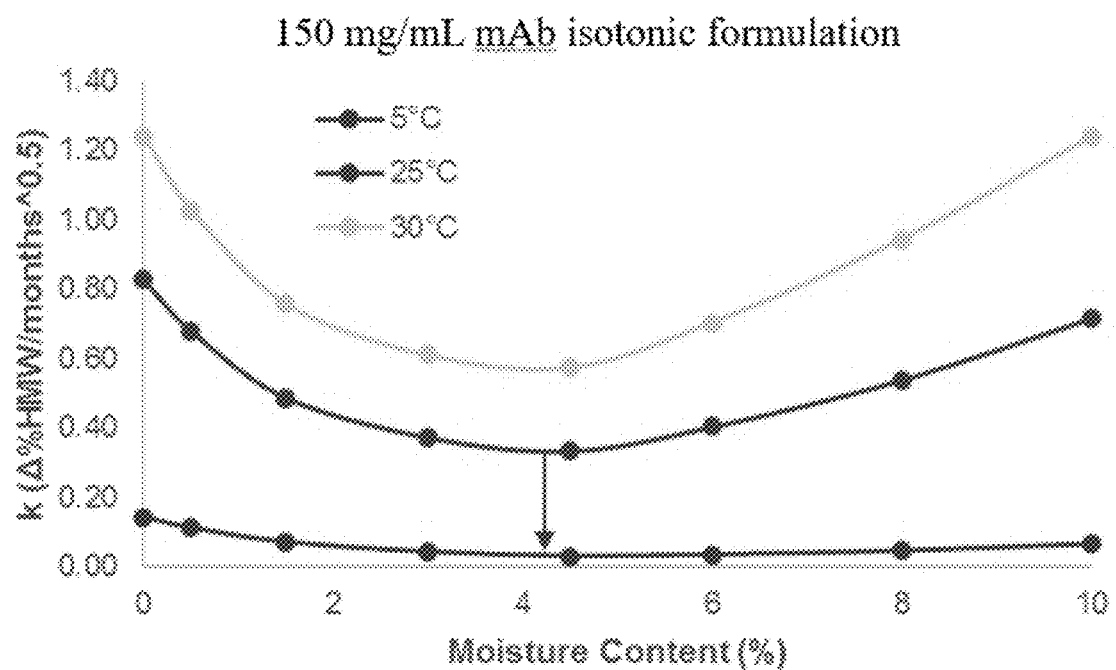
Figure 10:
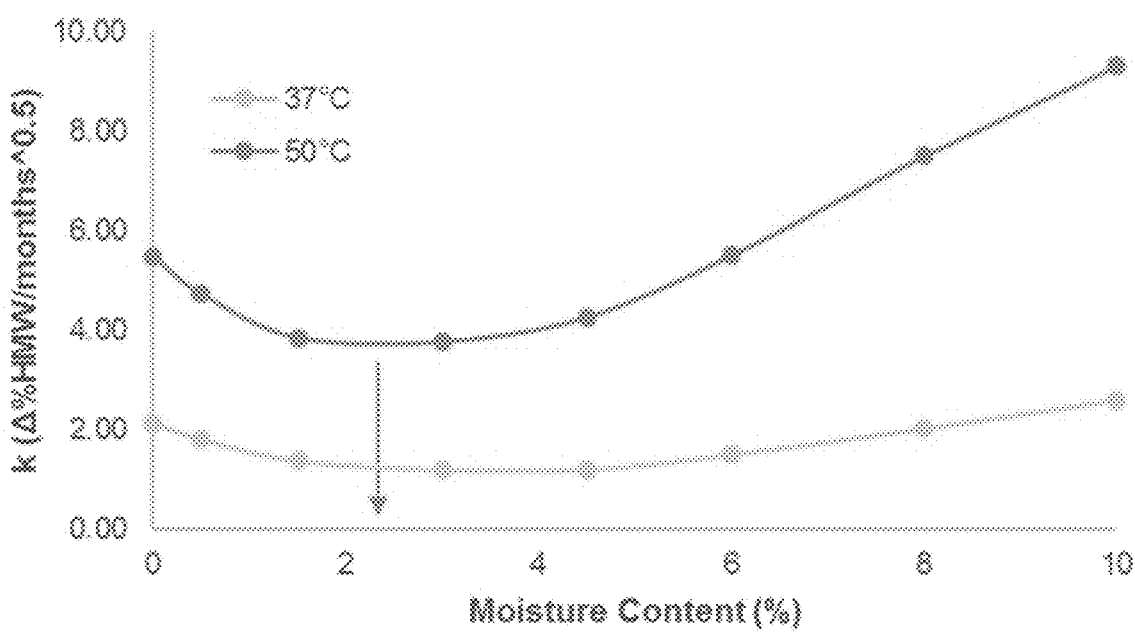

FIG. 10 shows the results of optimizing the moisture contents of the lyophilized cakes or lyophilized protein formulations according to an exemplary embodiment.

Figure 11:
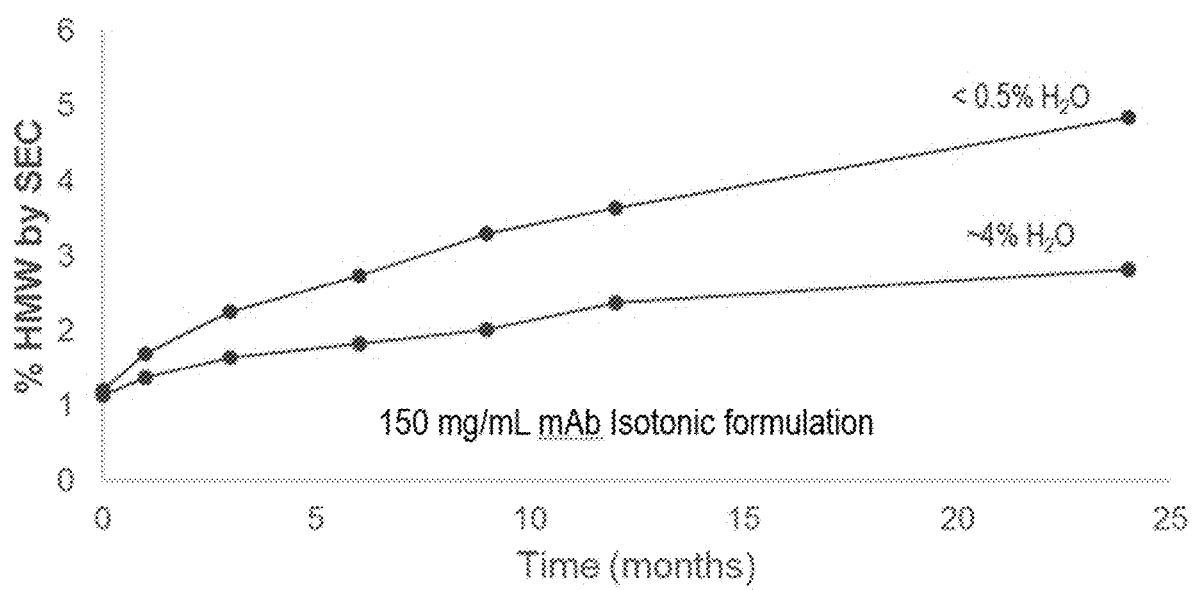

FIG. 11 shows the results of characterizing the stability of lyophilized cake or lyophilized protein formulation under optimal moisture content at about 4% at different time points, such as multiple time points in the time period of 0-25 months according to an exemplary embodiment. The experiments were conducted using 150 mg/mL mAb isotonic formulation under the storage condition of 25° C. by detecting the formation of HMW aggregations using a size exclusion column (SEC) according to an exemplary embodiment.

Figure 12:
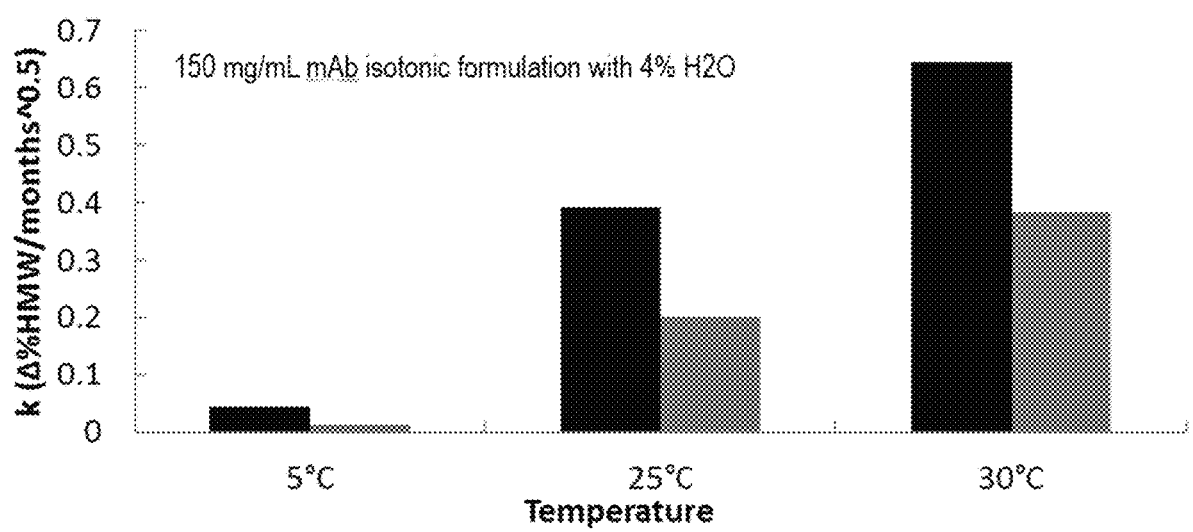

FIG. 12 shows the results of characterizing the stability of lyophilized cakes or lyophilized protein formulations after conducting post-lyophilization annealing under different storage temperatures, e.g., 5° C., 25° C. or 30° C., by detecting the formation of HMW aggregations according to an exemplary embodiment. The experiments were conducted using 150 mg/mL mAb isotonic formulation with 4% moisture content according to an exemplary embodiment.

Figure 13:
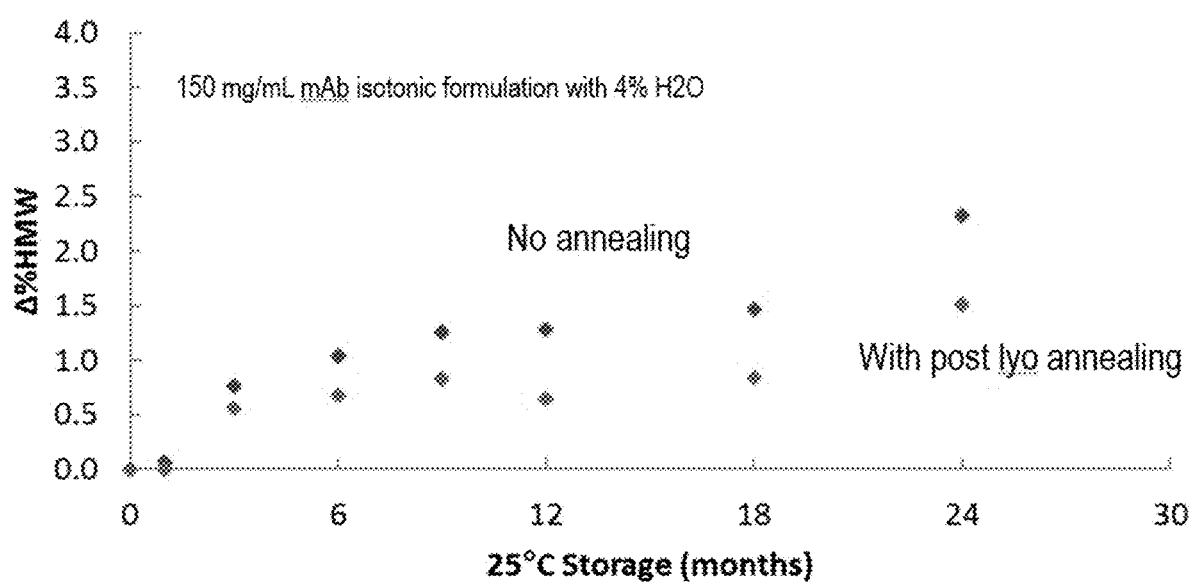

FIG. 13 shows the results of characterizing the stability of lyophilized cakes or lyophilized protein formulations after conducting post-lyophilization annealing under storage temperature at room temperature, e.g., 25° C., for 0-30 months according to an exemplary embodiment. The experiments were conducted using 150 mg/mL mAb isotonic formulation with 4% moisture content according to an exemplary embodiment.

DETAILED DESCRIPTION

There are various strategies to improve the stabilities of lyophilized protein (or peptide) formulations and to improve protein lyophilization processes, such as using cryo-protectants (lyo-protectants) to manage stress during freezing, using cryo-protectants to minimize drying stress, using bulking agents to improve cake appearance or using bulking agents to improve the lyophilization process, such as for easy lyophilization. For example, sucrose or trehalose is often selected to be incorporated in human lyophilized formulations, since sucrose and trehalose are disaccharides with good stabilization effects. Sucrose or trehalose can form an amorphous matrix to stabilize protein molecules in the solid state. However, the lyophilized protein formulation in the presence of sucrose or trehalose may have relatively low glass transition temperatures (Tg) and/or low collapse temperatures (Tc) that can cause challenges in the lyophilization process.

There are various factors to consider for designing protein formulations for early phase and late phase (commercialization) of protein drugs to achieve target product profiles, such as limitations of material and time, product knowledge, lyophilization cycle, formulation and stability as shown in Table 1. It is preferable to optimize a protein formulation which is isotonic and easy to lyophilize with elegant cake appearance. It is also preferable that the lyophilized cake has a short reconstitution time with low viscosity. In addition, for the purpose of commercial distribution and storage, it is preferable that the lyophilized cake or the lyophilized protein formulation has longer storage stability at 2-8° C. and/or at room temperature. It is highly preferable to have longer storage stability at room temperature to eliminate the requirement of refrigeration for late phase protein drug during commercial transportation and storage.

TABLE 1

Lyophilized protein formulation design strategies

| Factors to Consider | Early Phase | Late Phase/Commercial |
|---|---|---|
| Material and time limitations | More | Less |
| Product knowledge | Very limited | Good understanding |
| Lyophilization cycle | Conservative designs for different lyophilization units | Optimized/robust |
| Formulation | Preliminary | Optimized/Robust (isotonic, short reconstitution time/low viscosity, easy to lyophilize with elegant cake appearance) |
| Stability | 2°-8° C. storage for clinical supply | Longer storage stability for 2°-8° C. and room temperature for commercial distribution/storage with preference of stability at room temperature |

The present application provides formulation design strategies for early and late phase lyophilized protein (or peptide) formulations by applying different formulation strategies respectively to early or late phase lyophilized protein formulations. For example, in order to effectively stabilize the protein molecules, the excipient is preferably in the amorphous state, e.g., in the same amorphous state of the protein molecules. If the excipient is in a different state, such as in crystalline state, the excipient may separate from the protein molecules and that can lead to the loss of the stabilization effect.

In one aspect, the formulation design strategy of the present application provides cryo-protectants to manage stress during freezing, including using surfactants, sugars or amino acids as cryo-protectants. The cryo-protectants, stabilizers or bulking agents used in the formulation design strategies of the present application can include sugars, amino acids and salts. The sugars can include sucrose, trehalose, mannitol and sorbitol. The amino acids can include glycine, arginine, proline and histidine. The salts can include sodium chloride and arginine hydrochloride.

Since dehydration occurs during freezing, large degree of super-cooling can lead to large specific area of ice-water interface. Protein denaturation tends to occur on the ice-water interface. In one aspect, the formulation design strategy of the present application provides stabilizers to minimize drying stress, since dehydration of protein occurs during the lyophilization process, which can cause destabilization of the protein structure. The stabilizers provided by the formulation design strategy of the present application for minimizing drying stress include amino acids and hydrogen bond replacing agents, such as polyols including sucrose or trehalose. In addition, these stabilizers can prevent over-drying by preserving optimal residual moisture contents.

In one aspect, the formulation design strategy of the present application provides bulking agents for improving cake appearance and/or for easy lyophilization. The bulking agent is used to maintain a protein formulation with small solute contents, such as less than about 2%. The bulking agent can also be used to increase formulation Tc which is beneficial for protein formulations with low formulation Tc. Furthermore, the bulking agent, such as mannitol or glycine, can serve as crystalline excipient for easy lyophilization and for improving cake appearance. In one aspect, the bulk agents are preferably in a crystalline state in the lyophilized protein formulations, since lyophilized cake with crystalline bulk agents has elegant cake appearance. When mannitol or glycine is used as a bulk agent, it can improve the lyophilization process, e.g., easy to freeze-dry, since mannitol or glycine has high eutectic temperature. In some exemplary embodiments, the present application provides formulation design strategies to improve the lyophilization process including using crystalline bulking agents to increase formulation Tc. In some aspects, the preferred strategy is using mannitol and glycine as crystalline bulking agent to increase formulation Tc due to high eutectic temperature of mannitol or glycine (about 3° C.).

In one aspect, the present application provides formulation design strategies to improve the stabilities of the lyophilized protein formulations or the lyophilized cakes including using stabilizers, using the combinations of stabilizers and plasticizers, such as plasticizers with smaller molecular weights, or using post-lyophilization annealing. In one aspect, the present application provides formulation design strategies to manage formulation viscosities to reduce viscosities using viscosity reducers. In particular, formulations containing high protein concentration have high viscosities which can be effectively reduced using viscosity reducers.

In one aspect, the present application provides formulation design strategies to improve the stability of the lyophilized protein formulations or the lyophilized cakes for the late phase (commercialization) of drug products including increasing the concentrations of the stabilizers, using the combinations of stabilizers and plasticizers, and using post-lyophilization annealing. In addition, the present application provides strategies for increasing the moisture contents of the lyophilized protein formulations or lyophilized cakes to effectively improve stability of protein molecules, since water can serve as an effective plasticizer to immobilize the local mobility of protein molecules. The present application also provides formulation design strategies to produce lyophilized protein formulations or lyophilized cakes which have excellent stability under storage conditions at room temperature. The lyophilized protein formulations or lyophilized cakes which are stable at room temperature can provide the advantage of eliminating the requirement of refrigeration during commercial distribution and storage.

A relatively high content of residual moisture can serve as an effective plasticizer for lyophilized therapeutic proteins (e.g., therapeutic proteins in the "solid state"), which offers surprising stability to the protein for at least 24 months while stored at room temperature. In one aspect, a room-temperature stable lyophilized therapeutic protein formulation in a low mobility solid state having between 0.5 and 10 percent moisture is provided. In another aspect, a method of making room temperature stable, lyophilized therapeutic protein formulation is provided. In particular, residual moisture levels greater than 2%, greater than 3%, greater than 4%, greater than 5%, or greater than 6% in the lyophilization cake, but less than 10%, less than 8%, less than 7% or less than 6% allow annealing at relatively high temperatures for a prolonged period of time at room temperature. While not limited by any mechanism of action, the residual water content during the lyophilization process appears to permit alpha-relaxation to occur while preventing the formation of initial protein aggregates at relatively high concentrations of pharmaceutically formulation, preferably between 50-200 mg/ml, even more preferably between 100-150 mg/ml.

In one aspect, a pharmaceutically acceptable lyophilized cake comprising a stable protein, an excipient, and from about 0.5% to about 10% water, from about 3% to about 6% water, from about 4% to about 7% water, from about 5% to about 8% water, about 3%, about 4%, about 4.5%, or about 6% water by weight is provided. The protein of the pharmaceutically acceptable lyophilized cake remains stable for at least one month at room temperature, which can be 17-25° C., 20-25° C., or at about 25° C. "Stable" as used herein means in general that less than 5%, less than 4%, less than 3%, less than 2%, less than 1% or very little to none of the protein is degraded within 18 months of storage at room temperature. A common degradation pathway for proteins is the formation of aggregates and other HMW species. HMW species can be detected by many known methods, such as size exclusion chromatography and native or denatured electrophoretic gel mobility, preferably by size exclusion chromatography. Degradation also includes the formation of chemical products such as deamidated residues, reduced disulfide bonds, hydrolysis and peptide fragmentation, and the like, that can also be measured by methods known in the art.

In one embodiment, less than or equal to about 2% of the protein is degraded following 24 months of storage at about 25° C. Degradation can be determined by the changes of percentage of high molecular weight species as measured by size exclusion chromatography. The lower limit of detectable degradation with this method can be about 0.5% degradation, with about 0.2-0.3% as assay variability.

The pharmaceutically acceptable lyophilized cake can include one or more excipients in addition to the protein and the moisture. In one embodiment, the excipients include a buffer. That buffer can be any buffer that maintains the optimal pH for protein stability. Histidine is such a buffer, which has a pKa of about 6.0 and is capable of effectively buffering between pH 4.8 and 7.2. In some aspects, the excipient is histidine.

In one aspect, the excipients include a stabilizer. Stabilizers include various molecules such as polyols, sugars, amino acids, salts, or any combination thereof. Examples of useful stabilizers include sorbitol, glycerol, mannitol, trehalose, sucrose, arginine, alanine, proline, glycine, sodium chloride, or any combination thereof. In one aspect, the stabilizer makes up from about 19.9% to about 82.2% of the weight of the pharmaceutically acceptable lyophilized cake.

In one aspect, the stabilizer is only sucrose, and the stabilizer makes up from about 3% to about 15%, preferably about 5-11%, 4-7.5%, or 5-7.5% of the weight of the pharmaceutically acceptable lyophilized cake, depending on the presence of other stabilizer components and the amount of protein, water, and other excipients. In an aspect, the ratio of protein to stabilizer by weight is between 1:1-3:1, preferably 1.2:1-2:1, more preferably about 1.5:1.

In one aspect, the stabilizer includes sucrose combined with another stabilizing agent. Those other stabilizing agents combined with sucrose include any one or more of arginine, sorbitol, mannitol, glycerol, and alanine. In one aspect, the additional stabilizer comprises arginine, which may make up from about 4.83% to about 19.3% of the weight of the pharmaceutically acceptable lyophilized cake. In some aspects, the weight to weight ratio of sucrose to arginine ranges from about 3.2:1 to about 3.4:1. In another aspect, the additional stabilizer comprises sorbitol, which may make up from about 8.07% to about 22.4% of the weight of the pharmaceutically acceptable lyophilized cake. In another aspect, the additional stabilizer comprises mannitol, which may make up from about 8.07% to about 22.4% of the weight of the pharmaceutically acceptable lyophilized cake. In another aspect, the additional stabilizer comprises glycerol, which may make up from about 4.23% to about 12.7% of the weight of the pharmaceutically acceptable lyophilized cake. In yet another aspect, the additional stabilizer comprises alanine, which may make up from about 4.11% to about 12.4% of the weight of the pharmaceutically acceptable lyophilized cake.

In another aspect, the stabilizer comprises trehalose, which makes up from about 15.8% to about 70.2% of the weight of the pharmaceutically acceptable lyophilized cake, depending on the presence of other stabilizers and the amount of protein, water, and other excipients. In one aspect, the stabilizer comprises trehalose combined with another stabilizer. Those other stabilizers combined with trehalose include any one or more of arginine, sorbitol, mannitol, glycerol, and alanine. In one aspect, the additional stabilizer comprises arginine, which may make up from about 0.81% to about 14.3% of the weight of the pharmaceutically acceptable lyophilized cake. In another aspect, the additional stabilizer comprises sorbitol, which may make up from about 1.35% to about 22.4% of the weight of the pharmaceutically acceptable lyophilized cake. In another aspect, the additional stabilizer comprises glycerol, which may make up from about 0.69% to about 12.7% of the weight of the pharmaceutically acceptable lyophilized cake. In yet another aspect, the additional stabilizer comprises alanine, which may make up from about 0.69% to about 12.4% of the weight of the pharmaceutically acceptable lyophilized cake.

In another aspect, the excipients comprise a surfactant. The surfactant may comprise a nonionic detergent, such as a fatty acylated polyethoxylated sorbitan. In one aspect, the surfactant comprises a polysorbate generally, or specifically a polysorbate 80. In some aspects, the pharmaceutically acceptable lyophilized cake comprises from about 0.21% to about 0.96% surfactant, such as polysorbate 80, by weight.

In one aspect, the pharmaceutically acceptable lyophilized cake is manufactured by combining a protein, a buffer, a nonionic surfactant, and one or more stabilizers in water to make a pre-lyophilized aqueous solution. The solution is then freeze-dried to make a cake containing no more than 10% and no less than 0.5% moisture. The freeze-dried (lyophilized) protein is in a "solid state." In a particular aspect, the protein is a therapeutic recombinant human-like or humanized monoclonal antibody.

In one embodiment, the process includes the steps of obtaining an aqueous sample containing a protein and an excipient in a container. The container can be a vial, a syringe barrel, or a chamber of a dual chamber auto-injector. The container is sufficiently open to allow the outgassing of water vapor. The container containing the aqueous sample is placed into a chamber; heat is removed from the sample to attain a first temperature, wherein ice crystals form in the sample. Air is removed from the chamber to attain a first pressure. Thermal energy is then added to the sample to attain a second temperature to permit removal of the water from the sample by sublimation. Residual water may remain entrapped within the sample after sublimation, thereby requiring an additional second drying step. That second drying step is effectuated by adding thermal energy to the sample while maintaining the first pressure in the chamber, thereby attaining a third temperature. At that temperature, water is desorbed from the sample to attain a moisture level not greater than 10% and not less than 0.5%.

In one aspect during the initial freezing and primary drying step, heat is removed from the aqueous sample at a rate of about 0.5° C. per minute. In one aspect, the first temperature is about −45° C. In another aspect, the first temperature is held for about 60 minutes. In yet another aspect, the aqueous sample is held at 5° C. for about 30 minutes prior to attaining the first temperature.

In one aspect, the primary drying step is conducted at a second temperature of about −25° C. In one aspect, the second temperature is attained by increasing the shelf temperature at a rate of about 0.5° C. per minute. In one aspect, the second temperature is held for about 50 hours. In one aspect, the chamber pressure during primary drying is about 100 mTorr. In one aspect, the secondary drying step is conducted at a third temperature of about 35° C. In one aspect, the ramp rate for heating is about 0.3° C. per minute. In one aspect, the sample is held at the third temperature for about 6 hours. After secondary drying, in one aspect, the vial is stoppered at a chamber pressure of about 608,000 mTorr. In one aspect, the chamber is backfilled with $N_2$ gas prior to stoppering. In one aspect, the vial is stoppered with a Flurotec® coated 4432/50 butyl rubber lyophilization stopper.

In one aspect, the dried sample is annealed to relax the protein into a lower energy state and improve its overall stability. To anneal the sample, thermal energy is added to the sample to attain a fourth temperature. In some aspects, the sample is held at the fourth temperature for at least about 24 hours, at least about 48 hours, or at least about 60 hours to achieve the optimal effective relaxation (e.g., alpha and beta relaxation) of the protein. Once the protein has attained its optimal state of relaxation, the container is closed.

In one aspect, the fourth temperature, i.e., the annealing temperature is below the glass transition temperature of the sample after the water desorption step. In a specific aspect, the annealing temperature is about 70° C. In another specific aspect, the annealing temperature is about 45° C. In one aspect, the sample is maintained at the annealing temperature for about 72 hours. Since different proteins have distinct biophysical characteristics, in some aspects the fourth temperature is determined via modulated differential scanning calorimetry (MDSC). The calorimeter is charged with a lyophilized protein formulation sample, which has been through the secondary drying step. The sample is then subjected to incremental heating through the glass transition while heat flow is monitored. The Tg is determined. Samples are then held at various sub-Tg temperatures for various times to induce enthalpic relaxation of the molecules in the lyophilization cake. The relaxed samples are then subjected to DSC or MDSC and the peak area (heat capacity as a function of temperature) due to enthalpic recovery is determined (see Luthra el al., "Effects of annealing on enthalpy relaxation in lyophilized disaccharide formulations: mathematical modeling of DSC curves," 97(8) J Pharm Sci. 3084-99, 2008; and L. Thomas, "Modulated DSC® Paper #5: Measurement of Glass Transitions and Enthalpy Recovery," TA Instruments Publication TP 010, New Castle Del., available for download on the world wide web at tainstruments.com, accessed May 13, 2016). Those sub-Tg temperatures and times that provide optimal enthalpic relaxation can be selected for the fourth (e.g., annealing) temperature and time. See also W. Q., "Calorimetric analysis of cryopreservation and freeze-drying formulations," 1257 Methods Mol. Biol. 163-79 (2015).

An excipient is an ingredient added alongside an active drug substance in a pharmaceutical formulation. Excipients help to stabilize the drug substance and/or add bulk to the formulation. The term ingredient can be used interchangeably with excipients. Excipients include various substances for various purposes like buffering, bulking, solubilizing, stabilizing, plasticizing, and protecting the drug substance. Protectants protect against thermal stress and/or physical stress like agitation. Buffers are well known in the art. Excipients include stabilizers. A stabilizer can be added to the pre-lyophilized solution to stabilize the protein against aggregation or other degradation. Stabilization may occur via controlling the glass dynamics during the lyophilization process or by helping to preserve the native structure of the protein through specific interaction of the stabilizer with the protein. For a discussion of the biophysics of stabilizers during lyophilization, see Chang et al., "Mechanism of protein stabilization by sugars during freeze-drying and storage: native structure preservation, specific interaction, and/or immobilization in a glassy matrix?" 94(7) J. Pharm. Sci. 1427-44 (2005).

Stabilizers for inclusion in the pre-lyophilization solution include polyols, sugars, salts (e.g., sodium chloride), amino acids, and the like. Various individual stabilizers may be used alone or combined with one or more other stabilizers for optimal stabilizing effect. For example, a polyol may be combined with a sugar, a sugar with an amino acid, a polyol with an amino acid, a salt with a sugar, a salt with an amino acid, a salt with a polyol, and the like. Polyols are organic molecules with more than one hydroxyl groups (—OH). Polyols include monomers as well as polymers. Sugar alcohols are a subgroup of polyols sugar alcohols, which can serve as useful stabilizers, and include mannitol, xylitol, sorbitol, isomalt, erythritol, maltitol, and glycerol. Other monomeric polyols include ethylene glycol, propylene glycol and pentaerythritol. Polymeric polyols may be polyesters or polyethers of polyol subunits. Useful exemplar polymeric polyols include polypropylene glycol, polyethylene glycol, and poly (tetramethylene ether) glycol. Sugars can be used as stabilizers (as well as bulking agents). Sugars can be categorized as either reducing or non-reducing sugars. Non-reducing sugars include the disaccharides sucrose and trehalose. Reducing sugars include glucose, maltose, and lactose. Generally, non-reducing sugars are preferred for protein lyophilization, since reducing sugars may reduce proteins via the mallard reaction. See Lavakumar et al., "Lyophilization/Freeze Drying-A Review," 3(4) Int. J. Novel Trends in Pharm. Sci. 2277-2782 (2013). The disaccharides trehalose and sucrose are relatively inert and tend to form an amorphous glass during lyophilization. Trehalose or sucrose, either alone or in combination with an amino acid or polyol, is used as a stabilizer in the practice of this application.

Amino acids can be used as stabilizers. Glycine is a commonly used bulking agent and stabilizer. Other useful amino acids include arginine, alanine, and proline. In some aspects, arginine is used as a stabilizer. In some specific aspects, arginine is combined with sucrose, or arginine is combined with trehalose. In other aspects alanine is used as a stabilizer. In some specific aspects, alanine is combined with sucrose, or alanine is combined with trehalose.

In some exemplary aspects, one or more surfactants may be employed as an excipient. Surfactants are believed to provide additional stability by reducing protein-protein hydrophobic interaction and the resulting formation of high molecular weight species (i.e., aggregates). In some aspects, one or more surfactant(s) may be included in the pre-lyophilized protein-containing aqueous solution. In other aspects, one or more surfactant(s) may be included in the reconstitution diluent solution. Surfactants include substances which reduce the surface tension of a fluid in which it is dissolved and/or reduces the interfacial tension between oil and water. Surfactants can be ionic or non-ionic. Exemplary non-ionic surfactants that can be included in the pre-lyophilization solution or post reconstituted solution include, e.g., alkyl poly(ethylene oxide), alkyl polyglucosides (e.g., octyl glucoside and decyl maltoside), fatty alcohols such as cetyl alcohol and oleyl alcohol, cocamide MEA, cocamide DEA, and cocamide TEA. Specific non-ionic surfactants that can be included in the pre-lyophilized aqueous solution (or post reconstituted solution) include, e.g., polyoxyethylene sorbitan esters (a.k.a. polysorbates) such as polysorbate 20, polysorbate 28, polysorbate 40, polysorbate 60, polysorbate 65, polysorbate 80, polysorbate 81, and polysorbate 85; poloxamers such as poloxamer 188, poloxamer 407, polyethylene-polypropylene glycol; or polyethylene glycol (PEG). Polysorbate 20 is also known as TWEEN 20, sorbitan monolaurate and polyoxyethylenesorbitan monolaurate. Polysorbate 80 is also known as TWEEN 80, sorbitan monooleate and polyoxyethylenesorbitan monooleate.

One or more plasticizers can be included in the lyophilized protein composition. Plasticizers are generally used to increase the fluidity or flexibility of a system. It is thought that the increased fluidity is a result of the plasticizer increasing the free volume of the system and lowering the glass transition temperature. The addition of plasticizers modifies both alpha-relaxation and beta-relaxation within the lyophilized cake. Alpha-relaxation is also known as primary or glass relaxation and is a global relaxation process. Beta-relaxation is a more local process associated with protein polymer backbone motion that can be better modified by smaller molecules (i.e., plasticizers). Both relaxation processes reduce the overall energy of the system and, especially in the case of beta-relaxation, are thought to affect protein stability. It is generally known in the art of protein biophysics that plasticizers decrease beta-relaxation time and can concomitantly decrease protein stability (see e.g., Cicerone and Douglas, "β-Relaxation governs protein stability in sugar-glass matrices," Soft Matter 8: 2983-2991, 2012).

Useful plasticizers include polyols such as sorbitol, glycerol (glycerin), mannitol, and xylitol, amino acids such as glycine, arginine, proline, and alanine, and salts such as NaCl. Interestingly, water can also function as a plasticizer.

A lyophilized composition containing a protein and stabilizer forms a solid matrix, also known as a "cake" or "lyophilized cake." A "pharmaceutically acceptable cake" (also used interchangeably with or "pharmaceutically acceptable lyophilization cake") is amorphous (glassy, not crystalline) and has an aesthetically elegant appearance. The pharmaceutically acceptable cake should not show shrinkage, cracking, partial or total collapse, melt back, or discoloration. A red, black, brown, yellow, or other tinted cake is discolored and may be unacceptable. The preferred cake is mechanically strong and resistant to disruption during handling, porous and sponge-like, of uniform texture and forming a single entity, and uniformly white in color. The cake should be uniformly attached to the walls of the vial and not show detachment or other signs of shrinking. See Carpenter et al., "Rational design of stable lyophilized protein formulations: Some practical advice," Pharmaceutical Research, 14(8): 969-975, 1997.

The cake also should be free of visual defects due to freezing problems including chimney-like structures; dried foam on the upper surface area; crusting or glazing on the cake surface; and horizontal layering or ring formation. The cake should also be free of visual defects due to drying problems including shrinkage, where the cake volume is smaller than the frozen matrix and signs of wall detachment are apparent; cracking, where the cake shows fissures in the dry matrix and the cake does not form a single entity; different degrees of cake structure loss, such as total or partial collapse of the cake; melt back, where the cake contains a ring of dissolved material in the lower region; partial melt back, where only a small region in the base of the cake contains dissolved material; and browning, which is a yellow or brown discoloration of the cake due to the inclusion of reducing sugar that has undergone the Maillard reaction. Melt back is particularly problematic since it can lead to slow dissolution times, protein aggregation, degradation, and loss of potency. See FDA, "Guide to Inspections of Lyophilization of Parenterals (7/93). Finished product inspection. Last update 2009," 2009, last accessed Jul. 8, 2016 from http://wwwfda.gov/ICECl/Inspec-tions/Inspec-tionGuides/ucm074909.htm.

Exemplary embodiments disclosed herein satisfy the aforementioned demands by providing design strategies, methods and lyophilized protein formulations (lyophilized cakes) to satisfy the aforementioned demands by increasing the stabilities of the lyophilized protein formulations under room temperature storage condition.

The term "a" should be understood to mean "at least one"; and the terms "about" and "approximately" should be understood to permit standard variation as would be understood by those of ordinary skill in the art; and where ranges are provided, endpoints are included.

As used herein, the terms "include," "includes," and "including," are meant to be non-limiting and are understood to mean "comprise," "comprises," and "comprising," respectively.

In some exemplary embodiments, the disclosure provides a method of preparing a lyophilized cake, comprising: preparing a peptide or protein formulation and subjecting the peptide or protein formulation to lyophilization to produce a lyophilized cake; wherein the peptide or protein formulation comprises a peptide or a protein.

As used herein, the term "peptide" or "protein" includes any amino acid polymer having covalently linked amide bonds. Proteins comprise one or more amino acid polymer chains, generally known in the art as "peptide" or "polypeptides". A protein may contain one or multiple polypeptides to form a single functioning biomolecule.

In some exemplary embodiments, the peptide or protein is an antibody, an antibody fragment, a Fab region of an antibody, an antibody-drug conjugate, a fusion protein, a protein pharmaceutical product or a drug.

As used herein, an "antibody" is intended to refer to immunoglobulin molecules consisting of four polypeptide chains, two heavy (H) chains and two light (L) chains inter-connected by disulfide bonds. Each heavy chain has a heavy chain variable region (HCVR or VH) and a heavy chain constant region. The heavy chain constant region contains three domains, CH1, CH2 and CH3. Each light chain has of a light chain variable region and a light chain constant region. The light chain constant region consists of one domain (CL). The VH and VL regions can be further subdivided into regions of hypervariability, termed complementarity determining regions (CDR), interspersed with regions that are more conserved, termed framework regions (FR). Each VH and VL can be composed of three CDRs and four FRs, arranged from amino-terminus to carboxy-terminus in the following order: FR1, CDR1, FR2, CDR2, FR3, CDR3, FR4. The term "antibody" includes reference to both glycosylated and non-glycosylated immunoglobulins of any isotype or subclass. The term "antibody" is inclusive of, but not limited to, those that are prepared, expressed, created or isolated by recombinant means, such as antibodies isolated from a host cell transfected to express the antibody. An IgG comprises a subset of antibodies.

As used herein, an "antibody fragment" includes a portion of an intact antibody, such as, for example, the antigen-binding or variable region of an antibody. Examples of antibody fragments include, but are not limited to, a Fab fragment, a Fab' fragment, a F(ab')2 fragment, a Fc fragment, a scFv fragment, a Fv fragment, a dsFv diabody, a dAb fragment, a Fd' fragment, a Fd fragment, and an isolated complementarity determining region (CDR) region, as well as triabodies, tetrabodies, linear antibodies, single-chain antibody molecules, and multi specific antibodies formed from antibody fragments. Fv fragments are the combination of the variable regions of the immunoglobulin heavy and light chains, and ScFv proteins are recombinant single chain polypeptide molecules in which immunoglobulin light and heavy chain variable regions are connected by a peptide linker. An antibody fragment may be produced by various means. For example, an antibody fragment may be enzymatically or chemically produced by fragmentation of an intact antibody and/or it may be recombinantly produced from a gene encoding the partial antibody sequence. Alternatively or additionally, an antibody fragment may be wholly or partially synthetically produced. An antibody fragment may optionally comprise a single chain antibody fragment. Alternatively or additionally, an antibody fragment may comprise multiple chains that are linked together, for example, by disulfide linkages. An antibody fragment may optionally comprise a multi-molecular complex.

As used herein, the term "antibody-drug conjugate", or "ADC" can refer to antibody attached to biologically active drug(s) by linker(s) with labile bond(s). An ADC can comprise several molecules of a biologically active drug (or the payload) which can be covalently linked to side chains of amino acid residues of an antibody (Siler Panowski et al., Site-specific antibody drug conjugates for cancer therapy, 6 mAbs 34-45 (2013)). An antibody used for an ADC can be capable of binding with sufficient affinity for selective accumulation and durable retention at a target site. Most ADCs can have Kd values in the nanomolar range. The payload can have potency in the nanomolar/picomolar range and can be capable of reaching intracellular concentrations achievable following distribution of the ADC into target tissue. Finally, the linker that forms the connection between the payload and the antibody can be capable of being sufficiently stable in circulation to take advantage of the pharmacokinetic properties of the antibody moiety (e.g., long half-life) and to allow the payload to remain attached to the antibody as it distributes into tissues, yet should allow for efficient release of the biologically active drug once the ADC can be taken up into target cells. The linker can include: those that are non-cleavable during cellular processing and those that are cleavable once the ADC has reached the target site. With non-cleavable linkers, the biologically active drug released within the call includes the payload and all elements of the linker still attached to an amino acid residue of the antibody, typically a lysine or cysteine residue, following complete proteolytic degradation of the ADC within the lysosome. Cleavable linkers are those whose structure includes a site of cleavage between the payload and the amino acid attachment site on the antibody. Cleavage mechanisms can include hydrolysis of acid-labile bonds in acidic intracellular compartments, enzymatic cleavage of amide or ester bonds by an intracellular protease or esterase, and reductive cleavage of disulfide bonds by the reducing environment inside cells.

In some exemplary embodiments, the peptide or protein formulation further comprises a stabilizer, a cryo-protectant, a bulking agent, a plasticizer, or a combination thereof.

As used herein, the term "stabilizer" means at least one chemical entity that is not the buffer or the protein in a pharmaceutically acceptable lyophilized cake. In some embodiments, the term stabilizer means a combination of chemical entities (i.e., more than one chemical entity) that together serve to stabilize the protein or other macromolecule. For example, the stabilizer may be sucrose, or the stabilizer may be the combination of sucrose and arginine. In some embodiments, a larger molecular weight chemical entity, such as e.g. sucrose or trehalose, is paired with a smaller molecular weight chemical entity, such as e.g. arginine, proline, alanine, glycine, mannitol, sorbitol, and/or glycerol. The smaller chemical entity can increase mobility by enabling the protein to relax to a lower energy state.

In some exemplary embodiments, this disclosure provides a lyophilized cake prepared by the method of preparing a lyophilized cake of the present application. In some aspects, the lyophilized cake prepared by the method of the present application comprises about 3-5% water and is stable under the storage condition at room temperature.

The term "stable" or "stability" refers to the retention of an acceptable degree of physical structure (thermodynamic and colloidal stability), chemical structure (kinetic stability), or biological function (functional stability) of the protein after storage in a relevant environment or under certain conditions. The protein may be stable even though it does not maintain 100% of its physical structure, chemical structure, or biological function after storage for a certain amount of time. For example, a lyophilized protein can be considered stable when no more than 2% of the protein population is present in a high molecular weight form after storage at room temperature for up to 24 months. Stability can be measured by determining the percentage of native molecule that remains in a formulation after storage for a defined amount of time at a defined temperature or after delivery to a patient. The percentage of protein that retains its native form (e.g., the portion of native species relative to total protein, including high molecular weight and low molecular weight species) can be determined by size exclusion chromatography (e.g., size exclusion high performance liquid chromatography, SE-HPLC). In the case of a lyophilized protein, the cake is first solubilized and then the protein is subjected to testing. Native protein includes protein that is not aggregated or otherwise degraded. Stability can also be measured by determining the percentage of protein that forms an aggregate (e.g., high molecular weight species, a.k.a. BMW species) within the lyophilized cake after a defined amount of time at a defined temperature, wherein stability is inversely proportional to the percentage of BMW species that is formed. The percentage of BMW species of the protein may be determined by size exclusion chromatography after solubilization, as described above. A lyophilized protein composition may also be deemed stable if after three months at room temperature less than about 1%, 0.9%, 0.8%, 0.7%, 0.6%, 0.5%, 0.4%, 0.3%, 0.2% or 0.1% of the protein can be detected in a HMW form. Other methods may be used to assess the stability of the lyophilized protein such as, e.g., differential scanning calorimetry (DSC) to determine thermal stability, controlled agitation to determine mechanical stability, and absorbance at about 350 nm or about 405 nm to determine solution turbidities. For example, a formulation of the present invention may be considered stable if, after 6 or more months of storage at about 5° C. to about 25° C., the change in $OD_{405}$ of the formulation is less than about 0.05 (e.g., 0.04, 0.03, 0.02, 0.01, or less) from the $OD_{405}$ of the formulation at time zero.

EXEMPLARY EMBODIMENTS

Embodiments disclosed herein provide formulation design strategies and methods to produce lyophilized protein formulations or lyophilized cakes which have excellent stabilities under various storage conditions, such as at room temperature.

In some exemplary embodiments, this disclosure provides a method of preparing a lyophilized cake, comprising: preparing a peptide or protein formulation and subjecting the peptide or protein formulation to lyophilization to produce a lyophilized cake; wherein the peptide or protein formulation comprises a peptide or a protein. In some exemplary embodiments, the method of preparing a lyophilized cake further comprises subjecting the lyophilized cake to post-lyophilization annealing. In some exemplary embodiments, the peptide or protein formulation further comprises a stabilizer, a cryo-protectant, a bulking agent, a plasticizer, or a combination thereof.

In some aspects, the stabilizer, the cryo-protectant, the bulking agent or the plasticizer is surfactant, sugar, salt or amino acid. In some aspects, the sugar is sucrose, trehalose, mannitol or sorbitol. In some aspects, the amino acid is glycine, alanine, arginine, proline or histidine. In some aspects, the salt is sodium chloride or arginine hydrochloride.

In some exemplary embodiments, this disclosure provides a lyophilized cake prepared by the method of preparing a lyophilized cake of the present application. In some aspects, the lyophilized cake prepared by the method of preparing a lyophilized cake of the present application is stable under the storage condition at room temperature and comprises about 3-5% water, about 2-10% water, about 2-6% water, about 2-5% water, about 2-4.5% water, about 3-10% water, about 3-6% water, about 3-4.5% water, about 3.5-10% water, about 3.5-6% water, about 3.5-5% water, about 3.5-4.5% water, or preferable about 4% water.

It is understood that the method, the lyophilized protein formulation, or the lyophilized cake is not limited to any of the aforesaid lyophilization processes, stabilizers, cryo-protectants, bulking agents, plasticizers, antibodies, antibody-drug conjugates, protein pharmaceutical products or drugs.

The consecutive labeling of method steps as provided herein with numbers and/or letters is not meant to limit the method or any embodiments or aspects thereof to the particular indicated order. Various publications, including patents, patent applications, published patent applications, accession numbers, technical articles and scholarly articles are cited throughout the specification. Each of these cited references is incorporated by reference, in its entirety and for all purposes, herein. Unless described otherwise, all technical and scientific terms used herein have the same meaning as commonly understood by one of ordinary skill in the art to which this invention belongs. The disclosure will be more fully understood by reference to the following Examples, which are provided to describe the disclosure in greater detail. They are intended to illustrate and should not be construed as limiting the scope of the disclosure.

EXAMPLES

Material and Reagent Preparation

1. Lyophilization Cycle for Screening Stabilizers

For screening stabilizers (lyoprotectants), at least three steps were included in the lyophilization cycle, e.g., the steps of freezing, primary drying, and secondary drying. For the freezing step, the ramp rate for freezing was about 0.5° C./min and the length of freezing was about −45° C. for 60 minutes. For the primary drying step, the vacuum set point was about 100 mTorr, the ramp rate for heating was about 0.5° C./min, the temperature of primary drying was about −25° C., and the length of primary drying was about 50 hours. For the step of secondary drying, the vacuum set point was about 100 mTorr, the ramp rate for heating was 0.3° C./min, the temperature of secondary drying was about 35° C., and the length of secondary drying was about 6 hours.

Example 1. Screening Stabilizers for Formulations with Low Protein Concentration Various stabilizers (excipients) were added to the monoclonal antibody (mAb) formulations which had low protein concentrations, such as 2 mg/mL. The mAb formulations were subjected to lyophilization cycle for screening stabilizers of the present application. The screened stabilizers included sucrose, trehalose, sorbitol, mannitol, glycine, NaCl, arginine and alanine. The stabilities of the formulations were tested at storage condition of 50° C. for various time periods within 0-2 months by monitoring the formation of HMW aggregations. Several excipients, such as alanine, glycine or NaCl, showed destabilization effects as shown in FIG. 1. Several excipients, such as sucrose, trehalose or arginine showed stabilization effects. There were no detectable degradation of protein stability, such as the formation of HMW, when the lyophilized formulations, e.g., lyophilized cakes, in the presence of sucrose, trehalose or arginine were stored at 25° C. for 13 months. However, the lyophilized cake of the formulation containing arginine showing collapsed structure during the storage. It indicates that arginine is not suitable to be used alone as stabilizer for formulations with low protein concentrations.

The Tg and Tc of the lyophilized mAb formulations were determined using 2 mg/mL mAb isotonic formulations. As shown in Table 2, the stabilization effects of the stabilizers were not correlated with Tg or Tc. The results indicate that the destabilization effects may be caused by crystallization of the excipients, such as in the presence of glycine, proline, NaCl, mannitol or alanine. The results also indicate the observation of crystallization of the excipients, such as in the presence of mannitol, glycine, NaCl or alanine.

TABLE 2

Determinations of Tg and Tc for screening stabilizers for 2 mg/mL mAb isotonic formulation.

| Stabilizers | Δ % HMW at lyo/50° C. for 2 months | Tg (° C.) | Tc (partial) (° C.) | Tg' (° C.) |
|---|---|---|---|---|
| Sucrose | 0.2 | 58.8 | −28.0 (−32.2) | −34.1 |

TABLE 2-continued

Determinations of Tg and Tc for screening stabilizers for 2 mg/mL mAb isotonic formulation.

| Stabilizers | Δ % HMW at lyo/50° C. for 2 months | Tg (° C.) | Tc (partial) (° C.) | Tg' (° C.) |
|---|---|---|---|---|
| Trehalose | 0.3 | 119.9 | −28.5 (−30.5) | −31.3 |
| Arginine | 0.4 | Collapsed | −39.0 (−43.0) | −48.0 |
| None (Control) | 3.6 | Not Detectable | −23.5 (−29.0) | Not Detectable |
| Sorbitol | 9.0 | Collapsed | −39.1 (−43.5) | −46.7 |
| NaCl | 13.0 | Not Detectable | −25.5 (−27.2) | −46.3 |
| Glycine | 24.8 | Not Detectable | −4.0 (−10.0) | −46.8 |
| Mannitol | 31.8 | Not Detectable | −3.0 (−6.0) | −39.0 |
| Alanine | 34.6 | Not Detectable | −22.5 (−27.2) | −58.5 |
| Glycerol | 81.8 | Collapsed | −59.2 (−64.0) | −65.0 |

Figure 2:
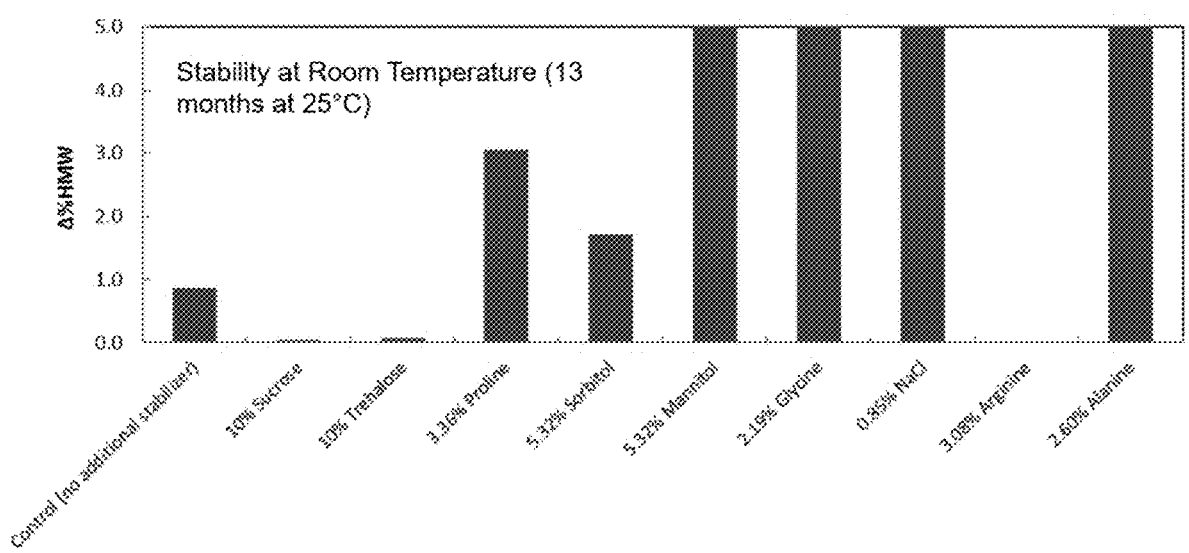

The stabilities of lyophilized mAb formulations containing various stabilizers were tested at room temperature using 2 mg/mL mAb formulations. As shown in FIG. 2, there were no detectable degradation of protein stability, such as the formation of HMW, for lyophilized 2 mg/mL mAb formulations in the presence of sucrose, trehalose or arginine for 13 months at 25° C. The lyophilized mAb formulations containing arginine showed collapsed structures for the storage of 13 month at 25° C. It indicates that arginine is not suitable to be used alone as stabilizer for mAb formulations with low protein concentration. The formation of BMW was the major degradation pathway for lyophilized mAb formulations at low protein concentration.

Figure 3:
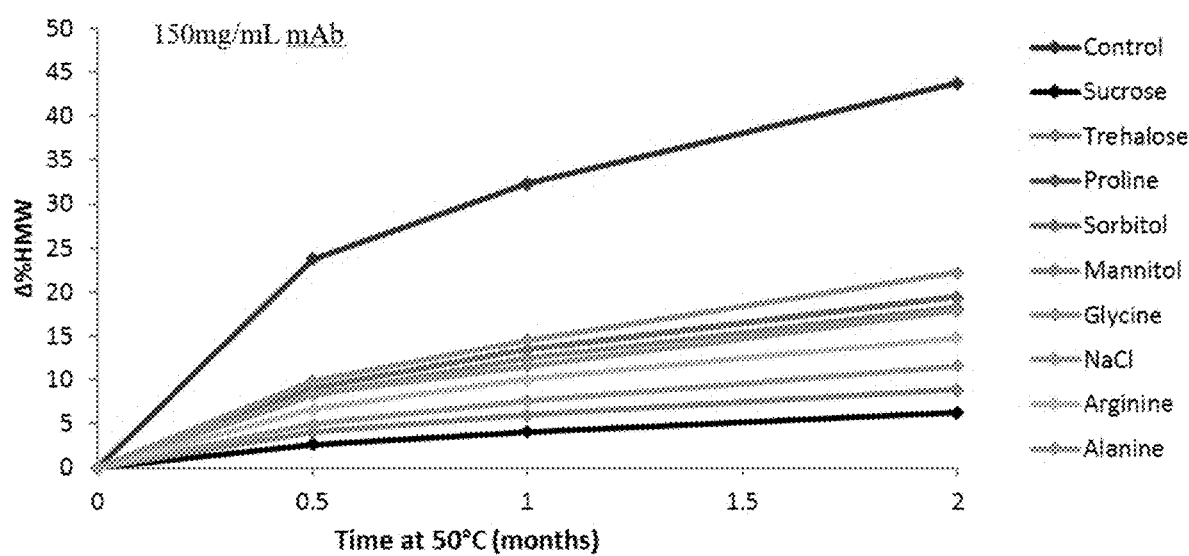

Example 2. Screening Stabilizers for Formulations with High Protein Concentration Various stabilizers were added to the mAb formulations which had high protein concentrations, such as 150 mg/mL. The mAb formulations were subjected to lyophilization cycle for screening stabilizers. The screened stabilizers included sucrose, trehalose, proline, sorbitol, mannitol, glycine, NaCl, arginine and alanine. The stabilities of the formulations were tested at storage condition of 50° C. for various time periods within 0-2 months by monitoring the formation of HMW aggregations. All of the tested stabilizers showed stabilization effects compared to the control formulation as shown in FIG. 3 for high protein concentration formulations. For the comparison of the tested results for low and high protein concentration formulations (FIG. 1 and FIG. 3), several stabilizers, such as sucrose, trehalose or arginine showed stabilization effects for both low and high protein concentration formulations. Several stabilizers, such as alanine, glycine or NaCl, showed destabilization effects for low protein concentration formulations as shown in FIG. 1. The test results indicate that the stabilizers behave differently in formulations with low or high protein concentrations.

The glass transition temperatures (Tg) and collapse temperatures (Tc) of the lyophilized mAb formulations were determined using 150 mg/mL mAb isotonic formulations. As shown in Table 3, the stabilization effects of the stabilizers were not correlated with Tg. The Tg were relatively high for all lyophilized formulations. Tc of the lyophilized mAb formulations were higher than Tg' of those, e.g., Tc' was about 15° C.−20° C. above Tg' as shown in Table 3. There was no observation of crystallization of the excipients (stabilizers) that indicated the presence of the excipients in amorphous state to stabilize the mAb. In addition, there was no observation of collapsed structure for the lyophilized cake of the mAb formulations. The results indicate that high protein concentration can contribute to the increases of Tc by preventing excipients from crystallization. The formation of BMW was monitored. Substantial increases of HMW (%) were observed, when the lyophilized formulations were stored at 25° C. for 4 months.

TABLE 3

Determinations of Tg and Tc for screening stabilizers for 150 mg/mL mAb isotonic formulations.

| Stabilizers | Δ % HMW at lyo/25° C. for 4 months | Tg (° C.) | TC (° C.) | Tg' (° C.) |
| --- | --- | --- | --- | --- |
| Sucrose | 1.3 | 113.4 | −3.5 | −24.2 |
| Mannitol | 2.0 | 104.6 | −1.5 | −28.1 |
| Trehalose | 2.1 | 140.9 | −5 | −22.6 |
| Sorbitol | 2.3 | 98.7 | −2.5 | −28.6 |
| Arginine | 3.7 | 105.5 | 0.0 | −23.6 |
| Glycine | 4.3 | 106.0 | −8.5 | −23.7 |
| Proline | 4.5 | 148.3 | −7.0 | −30.9 |
| Alanine | 4.6 | 103.5 | −4.2 | −30.8 |
| Glycerol | 5.8 | 105.3 | −13.5 | −30.2 |
| NaCl | 7.1 | 105.5 | −10.2 | −26.5 |
| None (Control) | 16.7 | Not Detectable | −0.5 | −18.3 |

Figure 4:
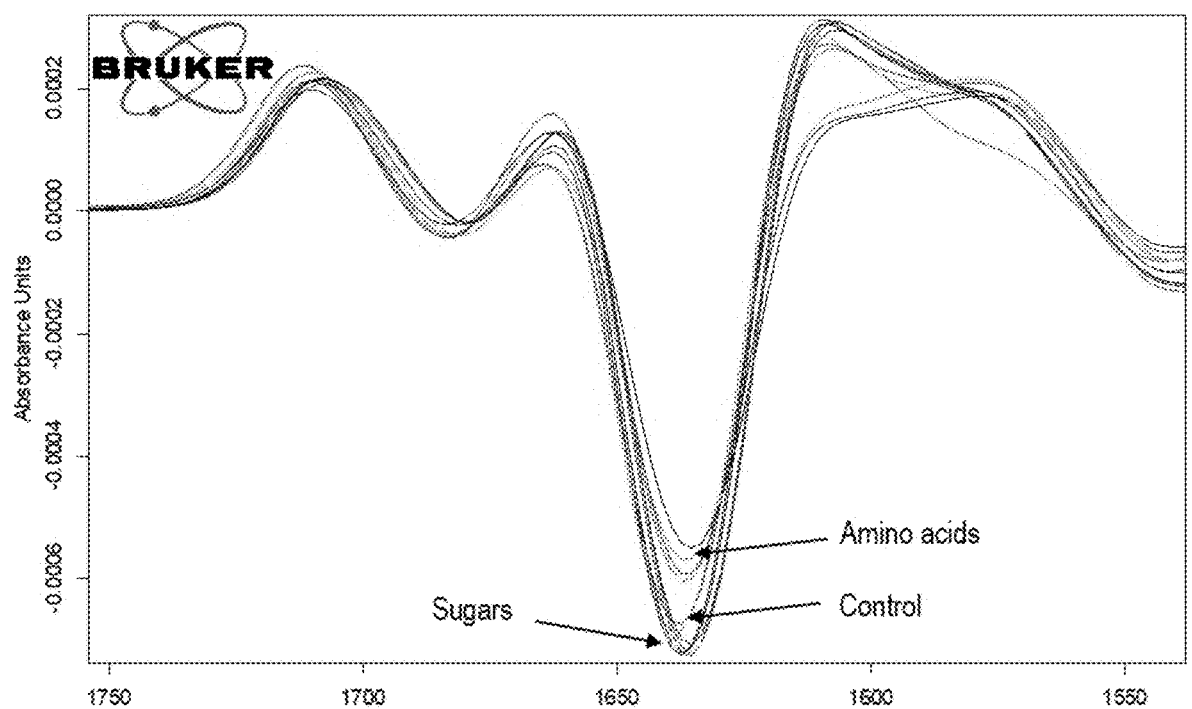

The lyophilized mAb formulations (150 mg/mL mAb formulations) in the presence of various stabilizers were subjected to the studies of protein conformation changes using FT-IR (Fourier transform infrared spectroscopy) spectrometer system from Bruker Optics Inc. The mAb preserved the secondary structures in the lyophilized formulations as shown in FIG. 4. The results indicates that the stabilization effects have some correlation with the solid state secondary structures of the mAb.

Example 3. Formulation Design Strategies for Early and Late Phase Lyophilized Protein Formulations The present application tested various formulation design strategies for early and late phase lyophilized protein (or peptide) formulations including using cryo-protectants to manage stress during freezing, such as using surfactants, sugars or amino acids as cryo-protectants; using stabilizers to minimize drying stress, including amino acids and hydrogen bond replacing agents, such as polyols (sucrose or trehalose); or using bulking agents for improving cake appearance and/or for easy lyophilization. In addition, bulking agents were used to maintain a protein formulation with small solute contents, such as less than about 2%. The crystalline bulking agent having high eutectic temperature, such as mannitol or glycine, was used to increase formulation Tc. Furthermore, the bulking agent, such as mannitol or glycine, was used as crystalline excipient for easy lyophilization and for improving cake appearance.

Various formulation design strategies were tested to improve the stabilities of the lyophilized protein formulations or the lyophilized cakes including using stabilizers, using the combinations of stabilizers and plasticizers, such as plasticizers with smaller molecular weights or using post lyophilization annealing. In addition, various formulation design strategies were tested to manage formulation viscosities to reduce viscosities of the high protein concentration formulations using viscosity reducers.

Example 4. Testing Various Concentrations of a Stabilizer

Figure 5:
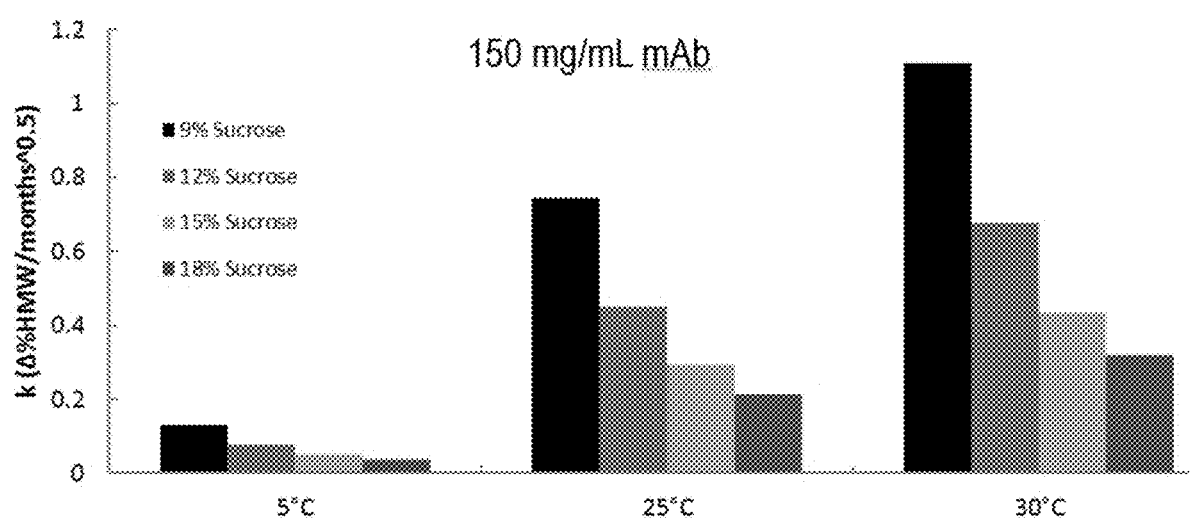

Various concentrations of sucrose were tested for improving the stabilities of the lyophilized protein formulations, e.g., protein formulations containing 150 mg/mL mAb. The stabilities of the lyophilized protein formulations were monitored by detecting the formation of BMW aggregations. The isotonic formulation contained 9% sucrose. Various sucrose concentrations including 9%, 12%, 15% and 18% sucrose were tested as shown in FIG. 5. The results indicate that the stabilities were increased in the presence of higher concentrations of sucrose. The presence of additional sucrose significantly increased the osmolality and viscosity of the mAb formulations.

Figure 6:
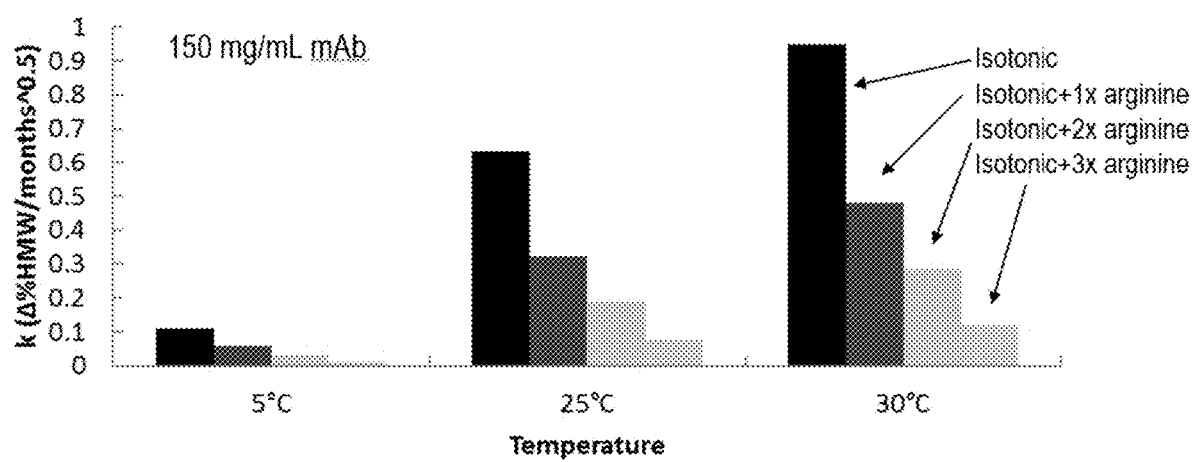

Example 5. Using Arginine to Improve Stabilities of Lyophilized Protein Formulations Various concentrations of arginine were incorporated to the mAb isotonic formulations for improving the stabilities of the lyophilized protein formulations, e.g., protein formulations containing 150 mg/mL mAb, as shown in FIG. 6. The stabilities of the lyophilized protein formulations were monitored by detecting the formation of HMW aggregations. The results indicate that the stabilities were increased in the presence of higher concentrations of arginine. The presence of additional arginine significantly increased the osmolality of the mAb formulations, but did not increase the viscosity of the mAb formulations.

Example 6. Optimizing the Ratio of Sucrose to Mannitol

Figure 7:
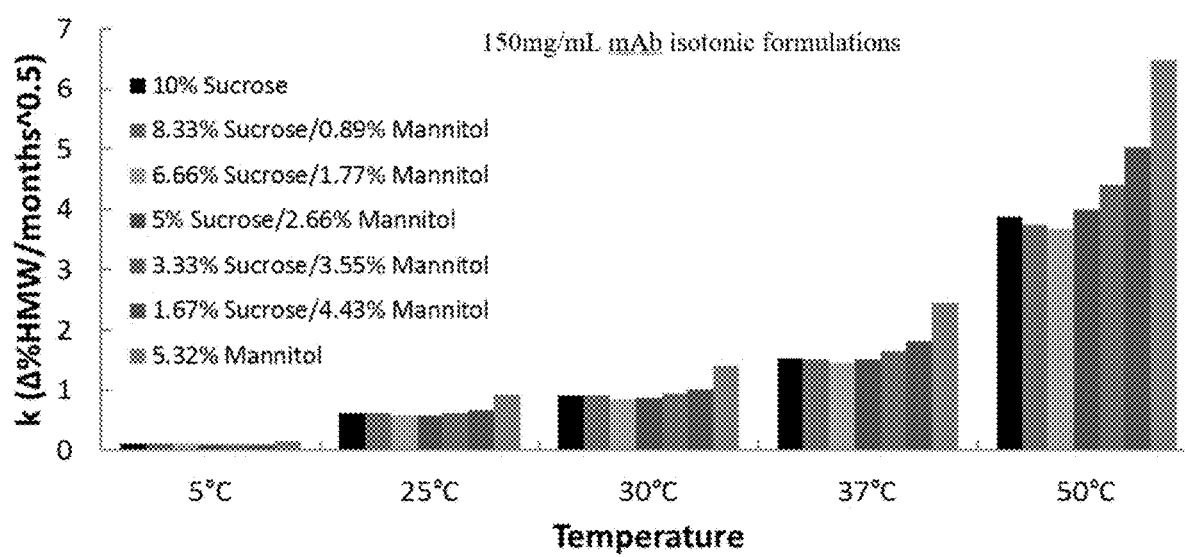

Sucrose and mannitol with various ratios were incorporated to the mAb isotonic formulations for improving the stabilities of the lyophilized protein formulations, e.g., protein formulations containing 150 mg/mL mAb, as shown in FIG. 7. The stabilities of the lyophilized protein formulations were monitored by detecting the formation of HMW aggregations at different storage temperatures. The results indicate that the optimal ratio of sucrose to mannitol can provide marginal stability improvement for high temperature storage. The results also indicate that the optimal ratio of sucrose to mannitol did not provide additional stability improvement for storage at room temperature or below room temperature.

Example 7. Optimizing the Ratio of Sucrose to Glycine

Figure 8:
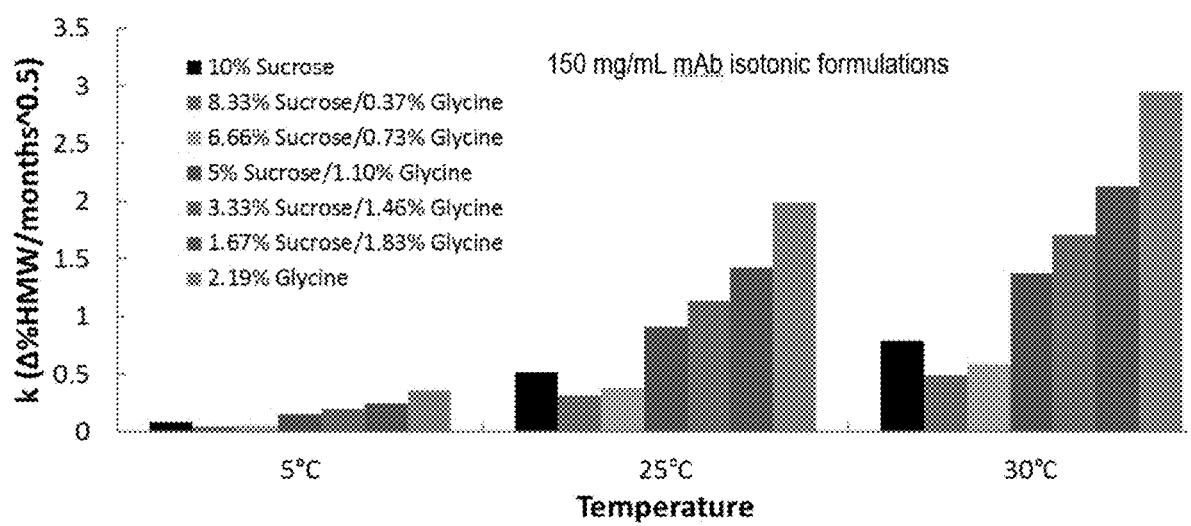

Sucrose and glycine with various ratios were incorporated to the mAb isotonic formulations for improving the stabilities of the lyophilized protein formulations, e.g., protein formulations containing 150 mg/mL mAb, as shown in FIG. 8. The stabilities of the lyophilized protein formulations were monitored by detecting the formation of HMW aggregations at different storage temperatures, such as 5° C., 25° C. or 30° C. The results indicate that the optimal ratio of sucrose to glycine can improve the stability of the lyophilized protein formulations without increasing the formulation osmolality. The results also indicate that sucrose is a more effective stabilizer compared to glycine at the same molar concentration, such as at about 300 mM.

An optimal ratio of sucrose to glycine was further selected for side-by-side comparison with 10% sucrose. The selected optima ratio of sucrose to glycine was 8.33% sucrose/0.37% glycine as shown in FIG. 9. MAB1 monoclonal antibody isotonic formulations at 150 mg/mL were prepared in 10 mM histidine, 0.1% polysorbate-80, pH 5.8 with 10% sucrose or with 8.33% sucrose/0.37% glycine. The experiments were conducted at 25° C. storage condition for 0-20 months by detecting the formation of HMW aggregations. The results indicate that the addition of trace amount of glycine can significantly improve the stabilities of the lyophilized protein formulations. Glycine can serve as a plasticizer which can immobilize local mobility of the protein molecules.

Example 8. Optimizing Moisture Contents

The lyophilized cake or lyophilized protein formulation with the least (e.g., driest) water content did not have the best stability under all storage conditions at 5° C. to 50° C. Therefore, experiments were conducted to optimize the moisture contents as shown in FIG. 10. The results indicate that about 4% (e.g., 3-5%) moisture content was optimal for room temperature storage. When the storage temperature was higher, such as at about 50° C., the optimal moisture content was relatively lower, such as at about 2.5%. When the moisture content was at optimal condition, there was no disadvantage of increasing formulation viscosity or osmolality.

The stability of lyophilized cake or lyophilized protein formation under optimal moisture content at about 4% was further characterized at different time points, such as multiple time points in the time period of 0-25 months as shown in FIG. 11. The experiments were conducted using 150 mg/mL mAb isotonic formulation under the storage condition of 25° C. by detecting the formation of HMW aggregations using size exclusion column (SEC). In comparing to the formulations with less than 0.5% moisture content, the formulations with about 4% moisture content exhibited improved stability under the storage condition at about 25° C. for at least about 25 months.

Example 9. Post-Lyophilization Annealing

Annealing was conducted after lyophilization on the lyophilized cakes or lyophilized protein formulations. Post-lyophilization annealing can be incorporated to the process as part of the lyophilization process. The optimization of the annealing condition can be conducted using mDSC (differential scanning calorimetry) for enthalpy recovery. The experiments were conducted using 150 mg/mL mAb isotonic formulation with 4% moisture content. After conducting the post-lyophilization annealing, the lyophilized cakes or lyophilized protein formulations were subjected to storage conditions at different temperatures, e.g., 5° C., 25° C. or 30° C., to test the stability by detecting the formation of HMW aggregations as shown in FIG. 12. The results indicate that conducting post-lyophilization annealing can significantly improve the stability of the lyophilized cakes or lyophilized protein formulations under all storage conditions, e.g., from 5° C. to 30° C.

The impacts of conducting post-lyophilization annealing were further investigated for room temperature storage condition. The experiments were conducted using 150 mg/mL mAb isotonic formulation with 4% moisture content. After conducting the post-lyophilization annealing, the lyophilized cakes or lyophilized protein formulations were subjected to storage conditions at room temperature, e.g., 25° C., for 0-30 months to test the stability by detecting the formation of HMW aggregations as shown in FIG. 13. The stabilities of lyophilized cakes with or without post-lyophilization annealing were compared side-by-side. The results indicate that conducting post-lyophilization annealing can further improve the stabilities of the lyophilized cakes or lyophilized protein formulations for room temperature storage.

What is claimed is:

1. A method of preparing a lyophilized cake, comprising: preparing a peptide or protein formulation, and subjecting the peptide or protein formulation to lyophilization to produce a lyophilized cake comprising a moisture content of about 4% by weight, about 5% sucrose by weight, and arginine in a weight to weight ratio of sucrose to arginine from about 3.2:1 to about 3.4:1;
wherein the peptide or protein formulation comprises a peptide or a protein.

2. The method of claim 1 further comprising subjecting the lyophilized cake to post-lyophilization annealing.

3. The method of claim 1, wherein the peptide or protein formulation further comprises a stabilizer, a cryo-protectant, a bulking agent, a plasticizer, or a combination thereof.

4. The method of claim 3, wherein the stabilizer is a hydrogen bond replacing agent.

5. The method of claim 3, wherein the cryo-protectant is surfactant, sugar, salt or amino acid.

6. The method of claim 3, wherein the bulking agent is mannitol, glycine or combinations thereof.

7. The method of claim 3, wherein the plasticizer is water or glycine.

8. The method of claim 3, wherein the bulking agent is in crystalline state in the lyophilized cake.

9. The method of claim 3, wherein the stabilizer or the cryo-protectant is in amorphous state in the lyophilized cake.

10. The method of claim 1, wherein the peptide or protein is an antibody, an antibody fragment, a Fab region of an antibody, an antibody-drug conjugate, a fusion protein, a protein pharmaceutical product or a drug.

11. The method of claim 3, wherein a concentration of the bulking agent is less than 2%.

12. The method of claim 1, wherein the concentration of the peptide or protein in the peptide or protein formulation is at least 100 mg/mL, wherein the peptide or protein formulation further comprises a viscosity reducer.

13. The method of claim 1, wherein the peptide or protein formulation is an isotonic formulation.

14. The method of claim 1, wherein the peptide or protein formulation of the lyophilized cake further comprises mannitol about 2.66% by weight.

15. The method of claim 1, wherein the peptide or protein formulation of the lyophilized cake further comprises glycine 1% glycine.

16. A lyophilized cake prepared by the method of claim 1.

* * * * *

UNITED STATES PATENT AND TRADEMARK OFFICE
CERTIFICATE OF CORRECTION

PATENT NO. : 11,241,498 B2  
APPLICATION NO. : 16/655634  
DATED : February 8, 2022  
INVENTOR(S) : Xiaolin Tang et al.

Page 1 of 1

It is certified that error appears in the above-identified patent and that said Letters Patent is hereby corrected as shown below:

On the Title Page

Item [73], insert:
--Regeneron Pharmaceuticals, Inc.
Tarrytown, NY (US)--

Signed and Sealed this
Twenty-sixth Day of July, 2022

Katherine Kelly Vidal
*Director of the United States Patent and Trademark Office*